(12) United States Patent
Melvin

(10) Patent No.: US 7,662,085 B2
(45) Date of Patent: Feb. 16, 2010

(54) PROTECTIVE SHEATH APPARATUS AND METHOD FOR USE WITH A HEART WALL ACTUATION SYSTEM FOR THE NATURAL HEART

(75) Inventor: David Boyd Melvin, Loveland, OH (US)

(73) Assignee: CardioEnergetics, Inc., Cincinnati, OH (US)

( * ) Notice: Subject to any disclaimer, the term of this patent is extended or adjusted under 35 U.S.C. 154(b) by 512 days.

(21) Appl. No.: 11/194,281

(22) Filed: Aug. 1, 2005

(65) Prior Publication Data

US 2006/0009676 A1 Jan. 12, 2006

Related U.S. Application Data

(62) Division of application No. 10/197,973, filed on Jul. 18, 2002, now abandoned.

(51) Int. Cl.
*A61M 1/10* (2006.01)
(52) U.S. Cl. .................................................... 600/16
(58) Field of Classification Search ................ 600/16, 600/17, 37; 601/153; 623/3.1, 3.11, 3.22, 623/3.17, 3.19, 3.23
See application file for complete search history.

(56) References Cited

U.S. PATENT DOCUMENTS

| | | | |
|---|---|---|---|
| 2,826,193 A | 3/1958 | Vineburg | |
| 3,053,249 A | 9/1962 | Smith | |
| 3,455,298 A | 7/1969 | Anstadt | |
| 3,513,836 A | 5/1970 | Sausse | |
| 3,590,815 A | 7/1971 | Schiff | |
| 3,613,672 A | 10/1971 | Schiff | |
| 3,668,708 A | 6/1972 | Tindal | |
| 3,713,439 A | 1/1973 | Cabezudo | |
| 3,827,426 A | 8/1974 | Page et al. | |
| 3,983,986 A | 10/1976 | Janke et al. | |
| 3,999,220 A | * 12/1976 | Keltner | ........................... 2/413 |
| 4,192,293 A | 3/1980 | Asrican | |
| 4,536,893 A | 8/1985 | Parravicini | |
| 4,621,617 A | 11/1986 | Sharma | |
| 4,690,134 A | 9/1987 | Snyders | |
| 4,846,831 A | 7/1989 | Skillin | |

(Continued)

FOREIGN PATENT DOCUMENTS

EP 019357 11/1980

(Continued)

*Primary Examiner*—Carl H Layno
*Assistant Examiner*—Frances P Oropeza
(74) *Attorney, Agent, or Firm*—Wood, Herron & Evans, LLP

(57) ABSTRACT

An actuation system for assisting the operation of the natural heart includes a framework for interfacing with a natural heart and which is coupled with tissue of the heart. An actuator element is adapted to be coupled to the framework and is configured for extending along a portion of a heart wall exterior surface. The actuator element is operable for deforming the portion of the heart wall to effect a reduction in the volume of the heart. A protective sheath is configured to extend along the heart wall between the actuator element and the heart wall portion for protecting the heart wall portion from damage by the actuator element. The protective sheath is flexible and operable to transmit, to the heart wall portion, a force thereon by the actuator element for indenting the heart wall portion.

17 Claims, 3 Drawing Sheets

U.S. PATENT DOCUMENTS

| | | |
|---|---|---|
| 4,904,255 A | 2/1990 | Chareire et al. |
| 5,109,843 A | 5/1992 | Melvin et al. |
| 5,119,804 A | 6/1992 | Anstadt |
| 5,131,905 A | 7/1992 | Grooters |
| 5,139,517 A | 8/1992 | Corral |
| 5,201,880 A | 4/1993 | Wright et al. |
| 5,256,132 A | 10/1993 | Snyders |
| 5,258,021 A | 11/1993 | Duran |
| 5,334,217 A | 8/1994 | Das |
| 5,358,519 A | 10/1994 | Grandjean |
| 5,370,685 A | 12/1994 | Stevens |
| 5,383,840 A | 1/1995 | Heilman et al. |
| 5,487,760 A | 1/1996 | Villafana |
| 5,533,958 A | 7/1996 | Wilk |
| 5,702,343 A | 12/1997 | Alferness |
| 5,713,954 A | 2/1998 | Rosenberg et al. |
| 5,800,528 A * | 9/1998 | Lederman et al. ............. 600/37 |
| 5,957,977 A | 9/1999 | Melvin |
| 6,183,411 B1 | 2/2001 | Mortier et al. |
| 6,332,864 B1 | 12/2001 | Schweich, Jr. et al. |
| 6,332,893 B1 | 12/2001 | Mortier et al. |
| 6,547,821 B1 | 4/2003 | Taylor et al. |
| 6,684,404 B2 | 2/2004 | Bachner, Jr. et al. |
| 6,808,483 B1 * | 10/2004 | Ortiz et al. .................... 600/16 |
| 2002/0007216 A1 * | 1/2002 | Melvin ...................... 623/3.11 |

FOREIGN PATENT DOCUMENTS

| | | |
|---|---|---|
| WO | WO 00/18320 | 4/2000 |
| WO | WO 01/67985 | 2/2001 |
| WO | WO 01/91667 | 12/2001 |

* cited by examiner

PROTECTIVE SHEATH APPARATUS AND METHOD FOR USE WITH A HEART WALL ACTUATION SYSTEM FOR THE NATURAL HEART

RELATED APPLICATIONS

This application is a Divisional application of U.S. patent application Ser. No. 10/197,973, filed Jul. 18, 2002 (now abandoned) and entitled "A Protective Sheath Apparatus and Method for Use with a Heart Wall Actuation System for the Natural Heart," which application is incorporated herein by reference in its entirety. In addition, this application is related to U.S. patent application Ser. No. 10/197,765, filed Jul. 18, 2002 (now abandoned) and entitled "A Flexible, Torsionable Cardiac Framework for Heart Wall Actuation of the Natural Heart, which is incorporated herein by reference in its entirety.

FIELD OF THE INVENTION

This invention relates generally to assisting the natural heart in operation by actuating a wall of the natural heart, and more specifically to facilitating such actuation without damage to the heart tissue.

BACKGROUND OF THE INVENTION

The natural human heart and accompanying circulatory system are critical components of the human body and systematically provide the needed nutrients and oxygen for operation of the body. As such, the proper operation of the circulatory system, and particularly, the proper operation of the heart, are critical in the life, health and well-being of a person. A physical ailment or condition which compromises the normal and healthy operation of the heart can therefore be particularly critical and may result in a condition which must be medically remedied.

More specifically, the natural heart, or rather the cardiac tissue of the heart, can degrade for various reasons to a point where the heart can no longer provide sufficient circulation of blood for maintaining the health of a patient at a desirable level. In fact, the heart may degrade to the point of failure and thereby may not even be able to sustain life. To address the problem of a failing natural heart, solutions are offered to provide ways in which circulation of blood might be maintained. Some solutions involve replacing the heart. Other solutions are directed to maintaining operation of the existing heart.

One such solution has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood. Such contact may enhance undesirable clotting of the blood, may cause a build-up of calcium, or may otherwise inhibit the blood's normal function. As a result, thromboembolism and hemolysis may occur. Additionally, the lining of an artificial heart or a ventricular assist device can crack, which inhibits performance, even when the crack is at a microscopic level. Such drawbacks have limited the use of artificial heart and assist devices to applications having too brief of a time period to provide a real lasting health benefit to the patient.

An alternative procedure also involves replacement of the heart, but includes a transplant of a natural heart from another human or animal into the patient. The transplant procedure requires removing an existing organ (i.e. the natural heart) from the patient for substitution with another organ (i.e. another natural heart) from another human, or potentially, from an animal. Before replacing an existing organ with another, the substitute organ must be "matched" to the recipient, which can be, at best, difficult, time consuming, and expensive to accomplish. Furthermore, even if the transplanted organ matches the recipient, a risk exists that the recipient's body will still reject the transplanted organ and attack it as a foreign object. Moreover, the number of potential donor hearts is far less than the number of patients in need of a natural heart transplant. Although use of animal hearts would lessen the problem of having fewer donors than recipients, there is an enhanced concern with respect to the rejection of the animal heart.

Rather than replacing the patient's heart, other solutions attempt to continue to use the existing heart and associated tissue. In one such solution, attempts have been made to wrap skeletal muscle tissue around the natural heart to use as an auxiliary contraction mechanism so that the heart may pump. As currently used, skeletal muscle cannot alone typically provide sufficient and sustained pumping power for maintaining circulation of blood through the circulatory system of the body. This is especially true for those patients with severe heart failure.

Another system developed for use with an existing heart for sustaining the circulatory function and pumping action of the heart, is an external bypass system, such as a cardiopulmonary (heart-lung) machine. Typically, bypass systems of this type are complex and large, and, as such, are limited to short term use, such as in an operating room during surgery, or when maintaining the circulation of a patient while awaiting receipt of a transplant heart. The size and complexity effectively prohibit use of bypass systems as a long term solution, as they are rarely portable devices. Furthermore, long term use of a heart-lung machine can damage the blood cells and blood borne products, resulting in post surgical complications such as bleeding, thromboembolism function, and increased risk of infection.

Still another solution for maintaining the existing natural heart as the pumping device involves enveloping a substantial portion of the natural heart, such as the entire left and right ventricles, with a pumping device for rhythmic compression. That is, the exterior wall surfaces of the heart are contacted and the heart walls are compressed to change the volume of the heart and thereby pump blood out of the chambers. Although somewhat effective as a short term treatment, the existing pumping devices have not been suitable for long term use.

Typically, with such compression devices, heart walls are concentrically compressed. A vacuum pressure is then needed to overcome cardiac tissue/wall stiffness, so that the compressed heart chambers can return to their original volume and refill with blood. This "active filling" of the chambers with blood limits the ability of the pumping device to respond to the need for adjustments in the blood volume pumped through the natural heart, and can adversely affect the circulation of blood to the coronary arteries. Furthermore, natural heart valves, between the chambers of the heart and leaching into and out of the heart, are quite sensitive to wall distortion and annular distortion. The compressive movement patterns that reduce a chamber's volume and distort the heart walls may not necessarily facilitate valve closure (which can lead to valve leakage).

Therefore, mechanical pumping of the heart, such as through mechanical compression or distortion of the ventricles, must address these issues and concerns in order to establish the efficacy of long term mechanical or mechanically-assisted pumping. Specifically, the ventricles must rapidly and passively refill at low physiologic pressures, and the valve functions must be physiologically adequate. The myocardial blood flow of the heart also must not be impaired by the mechanical device. Still further, the left and right ventricle pressure independence must be maintained within the heart.

The present invention addresses the issues of heart wall stiffness and the need for active refilling by assisting in the bending (i.e., indenting, flattening, twisting, etc.) of the heart walls, rather than concentrically compressing the heart walls. Because of the mechanics of deformation in hearts having proportions typical in heart failure (specifically, wall thickness/chamber radius ratios), the deformation from bending and the subsequent refilling of the heart requires significantly less energy than would the re-stretching of a wall that has been shortened to change the chamber volume a similar amount. The present invention facilitates such desirable heart wall bending and specifically protects the heart wall during such bending.

Another major obstacle with long term use of such pumping devices is the deleterious effect of forceful contact of different parts of the living internal heart surface (endocardium), one against another, due to lack of precise control of wall actuation. In certain cases, this coaptation of endocardium tissue is probably necessary for a device that encompasses both ventricles to produce independent output pressures from the left and right ventricles. However, it can compromise the integrity of the living endothelium.

Mechanical ventricular wall actuation has shown promise, despite the issues noted above. As such, devices have been invented for mechanically assisting the pumping function of the heart, and specifically for externally actuating a heart wall, such as a ventricular wall, to assist in such pumping functions.

Specifically, U.S. Pat. No. 5,957,977, which is incorporated herein by reference in its entirety, discloses an actuation system for the natural heart utilizing internal and external support structures. That patent discloses an internal and external framework mounted internally and externally with respect to the natural heart, and an actuator element or activator mounted to the framework for providing cyclical forces to deform one or more walls of the heart, such as the left ventricular wall. The invention of U.S. patent application Ser. No. 09/850,554, which is also incorporated herein by reference in its entirety, further adds to the art of U.S. Pat. No. 5,957,977 and specifically sets forth various embodiments of activators or actuator elements which are suitable for deforming the heart walls and supplementing and/or providing the pumping function for the natural heart.

The actuation provided by such systems uses mechanical elements which engage, act upon and shape a portion of a heart wall. The heart wall is living tissue and, therefore, a concern with such heart wall actuation systems is the prevention of damage to the heart tissue during actuation. Specifically, it is desirable to prevent significant trauma to the outer tissue surfaces of the heart walls acted upon by the actuator elements.

It is therefore an objective of the present invention to further assist in the operation of such systems with the natural heart.

Specifically, it is an objective of the invention to prevent damage to the tissue of the heart, and particularly to prevent damage to the outer heart surface due to abrasion, pinching or other trauma to the heart associated with a heart wall actuation system.

It is still another objective of the present invention to provide long term actuation and assistance for the heart by reducing friction on the heart wall from a heart wall actuation system.

It is a further objective of the present invention to encourage the creation of a layer of flexible fibrous or scar tissue on the heart for further protection of the heart with a heart wall actuation system.

These objectives and other objectives are addressed by the invention as described and claimed below.

SUMMARY OF THE INVENTION

An actuation system for assisting the operation of the natural heart includes a framework for interfacing with the natural heart, an actuator element adapted to be coupled to the framework, and a protective sheath which is configured to extend along the heart wall between the actuator element and a heart wall portion for protecting the heart wall from damage by the action of the actuator element. More specifically, a framework interfaced with the natural heart includes elements which are configured for being anchored to tissue of the heart. An actuator element is configured to extend along a portion of the heart wall exterior surface and indent a portion of the heart wall to effect a reduction in the volume of one or more chambers of the heart and assist its pumping action.

Such movement along the heart wall and the forces introduced by the actuator element may provide friction, abrasion, pinching, or other trauma to the heart wall, and specifically to the tissue of the outer surface of the heart. The invention utilizes a protective sheath to extend along the heart wall between the actuator element and absorb any abrasion, pinching, or friction forces of the actuator element, to thereby prevent damage to the heart. The protective sheath is flexible and is operable to transmit, to the actuated heart wall portion, a force thereon for indenting the heart wall portion. That is, the forces of the actuator element generally tangent to the heart wall are absorbed, while those forces having components which are normal to the heart wall are transmitted for indenting the heart wall portion and assisting the pumping function of the heart by reducing the volume of one or more heart chambers.

In one embodiment of the invention, the protective sheath is a porous sheath formed by a plurality of interlocking elements formed of an abrasion-resistant material, such as a metal material, or an abrasion-resistant polymer. The interlocked elements may be utilized to form ring-shaped structures, such as to provide a "chain-mail effect" over the surface of the heart.

In another embodiment of the invention, the protective sheath includes a fabric jacket with a plurality of studs interspersed throughout the fabric. The stud surfaces are generally co-extensive with the surfaces of the fabric. The studs have rounded surfaces on at least one surface of the fabric, such as the one positioned outwardly from the heart surface and which is engaged by an actuator element. In that way, the protective sheath provides smooth operation of the actuator element against the heart wall, while preventing damage to the heart wall and translating forces from the actuator element to the chamber which is being actuated. The studs are formed of a suitable rugged and wear-resistant material, such as a metal, ceramic, or an abrasion-resistant polymer.

In still another embodiment of the invention, the protective sheath includes a net of woven, abrasion-resistant cords which are intermeshed to form the sheath. The cords forming the net are made of a suitable abrasion-resistant material such as metal, or an abrasion-resistant polymer.

Further features and benefits of the invention are set forth hereinbelow in the Detailed Description of Embodiments of the Invention.

BRIEF DESCRIPTION OF THE FIGURES

The accompanying drawings, which are incorporated in and constitute a part of this specification, illustrate embodiments of the invention and, together with a general description of the invention given below, serve to explain the principles of the invention.

DETAILED DESCRIPTION OF EMBODIMENTS OF THE INVENTION

The present invention may best be described in the context of the natural human heart, and accordingly, the heart structure is discussed briefly herein. Furthermore, the present invention is utilized in conjunction with a heart wall actuation system. One such actuation system, is described in U.S. patent application Ser. No. 09/850,554, which application is incorporated herein by reference in its entirety. Another suitable actuation system for practicing the invention is disclosed in greater detail in U.S. Pat. No. 5,957,977, which patent is incorporated herein by reference in its entirety. Other actuation systems may also be suitable. A brief overview of one type of actuation system for practicing the invention and of a framework for such a system is set forth herein.

Figure 1A:
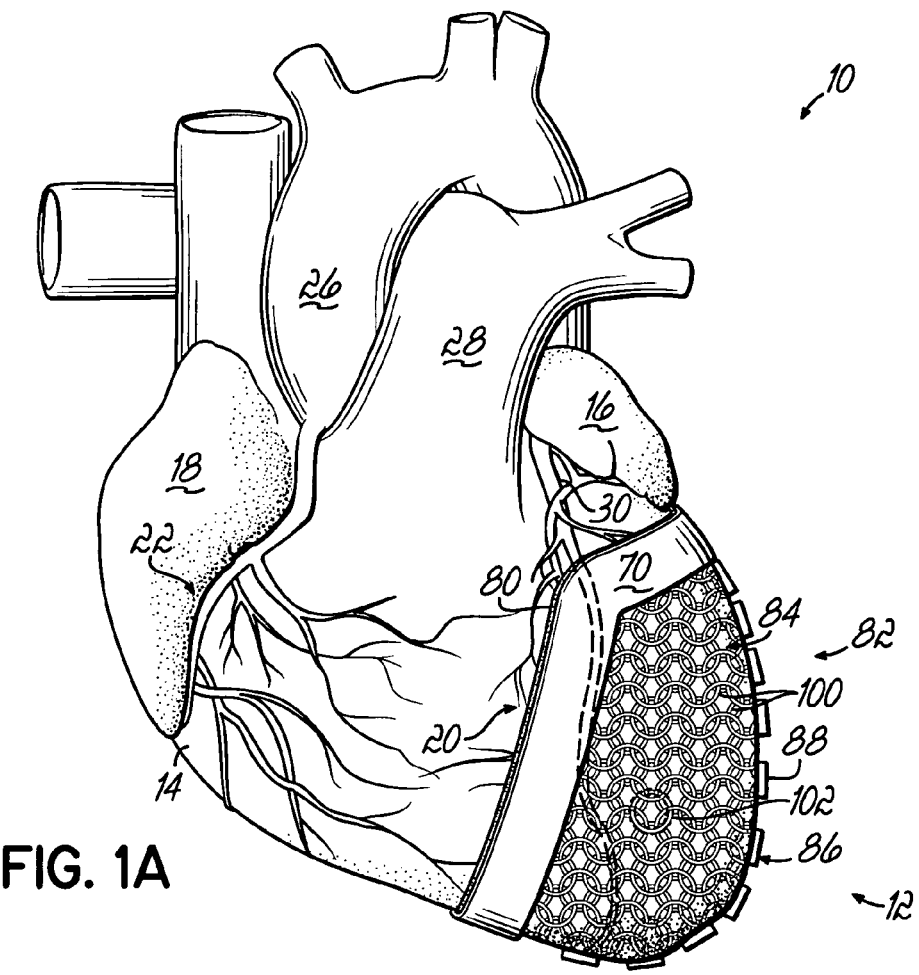
FIG. 1A is a perspective view of one embodiment of the invention illustrated on a natural human heart.
Figure 2A:
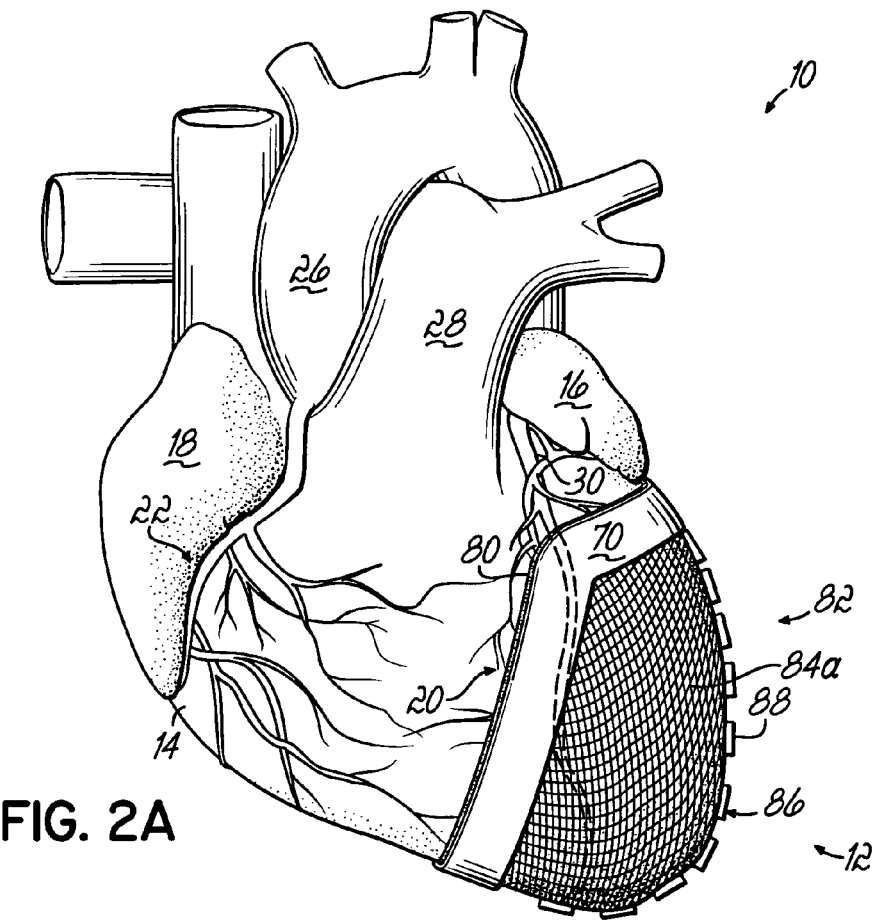
FIG. 2A is a perspective view of an alternative embodiment of the invention illustrated on a natural human heart.
Figures 3A, 3B, 3C:
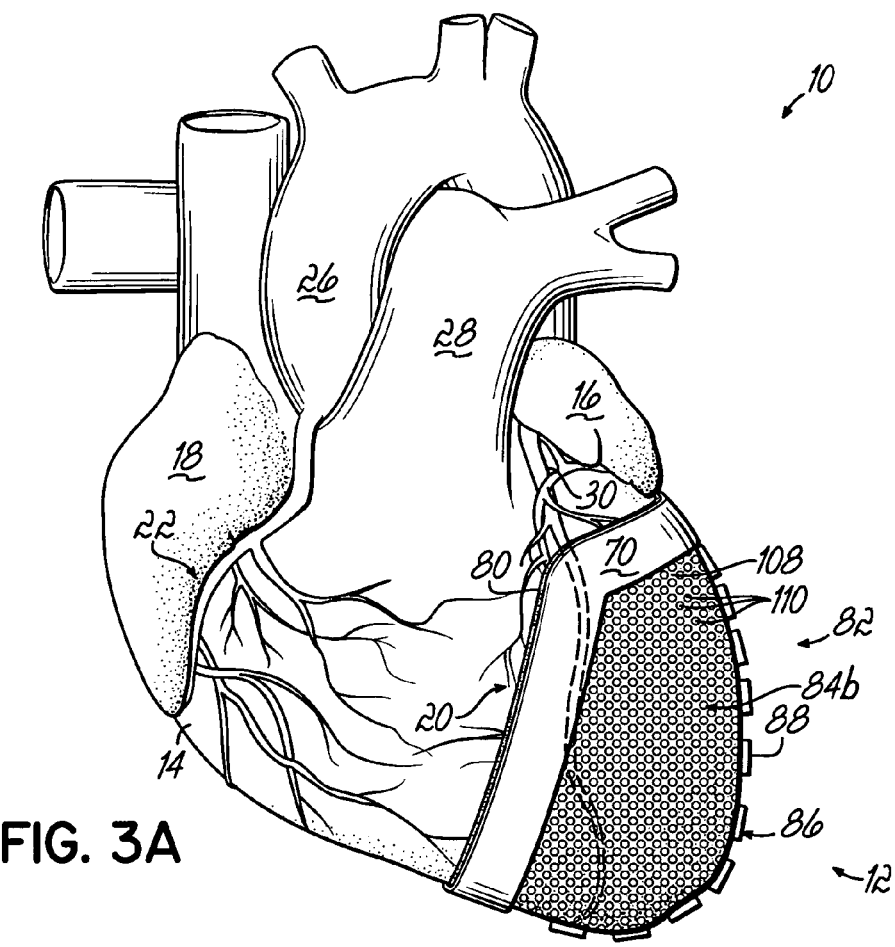
FIG. 3A is a perspective view of another alternative embodiment of the invention illustrated on a natural human heart.
FIGS. 3B and 3C are cross-sectional views which illustrate the alternative embodiment of the invention shown in FIG. 3A with a heart wall actuation system in a relaxed and an actuated state, respectively.

An understanding of the heart is helpful in understanding the invention, and the heart and various of its components are described herein. Referring now to FIGS. 1A, 2A and 3A, a natural human heart 10 is shown in perspective with a portion of a framework of a suitable actuation system and various embodiments of protective sheaths. Heart 10 has a lower portion comprising two chambers, namely a left ventricle 12 and a right ventricle 14, which function primarily to supply the main pumping forces that propel blood through the circulatory system, including the pulmonary system (lungs) and the rest of the body, respectively. Heart 10 also includes an upper portion having two chambers, a left atrium 16 and a right atrium 18, which primarily serve as entryways to the ventricles 12 or 14, and also assist in moving blood into the ventricles 12 or 14. The interventricular wall or septum of cardiac tissue separating the left and right ventricles 12 and 14, is defined externally by an interventricular groove 20 on the exterior wall of the natural heart 10. The atrioventricular-wall of cardiac tissue separating the lower ventricular region from the upper atrial region is defined by atrioventricular groove 22 on the exterior wall of the natural heart 10. The configuration and function of the heart is known to those of ordinary skill in this art.

Generally, the ventricles are in fluid communication with their respective atria through an atrioventricular valve in the interior volume defined by heart 10. More specifically, the left ventricle 12 is in fluid communication with the left atrium 16 through the mitral valve, while the right ventricle 14 is in fluid communication with the right atrium 18 through the tricuspid valve. Generally, the ventricles are in fluid communication with the circulatory system (i.e., the pulmonary and peripheral circulatory system) through semilunar valves. More specifically, the left ventricle 12 is in fluid communication with the aorta 26 of the peripheral circulatory system, through the aortic valve, while the right ventricle 14 is in fluid communication with the pulmonary artery 28 of the pulmonary, circulatory system through the pulmonic or pulmonary valve.

The heart basically acts like a pump. The left and right ventricles are separate, but share a common wall, or septum. The left ventricle has thicker walls and pumps blood into the systemic circulation of the body. The pumping action of the left ventricle is more forceful than that of the right ventricle, and the associated pressure achieved within the left ventricle is also greater than in the right ventricle. The right ventricle pumps blood into the pulmonary circulation, including the lungs. During operation, the left ventricle fills with blood in the portion of the cardiac cycle referred to as diastole. The left ventricle then ejects any blood in the part of the cardiac cycle referred to as systole. The volume of the left ventricle is largest during diastole, and smallest during systole. The heart chambers, particularly the ventricles, change in volume during pumping.

By way of a non-limiting example, the present invention is discussed in terms of use with a heart wall actuation system to assist in the actuation and operation of the left ventricular portion of the heart 10. However, it is noted that the present invention can also be used for the actuation and operation of other portions of the natural heart 10, such as the individual atria, the right ventricular portion of the heart 10, or simultaneously both atria or both ventricles. The present invention protects the portion of the heart engaged by an actuation system.

In accordance with illustrating an example of use of the invention with the left ventricular portion of the heart, a framework is discussed which positions one possible actuator system on the exterior surface or epicardium of the left ventricle. The invention may also be used on other surfaces of the heart. Also, other actuation systems may be used with the invention other than the one illustrated in the drawings.

Part of the framework is illustrated in FIGS. 1A, 2A, and 3A by reference numeral 70, which refers to an external component or yoke of the framework. The framework also includes internal framework elements (not shown) including an internal stint to which the external yoke or external framework element 70 is fixed by transmural cords which extend through walls of the heart. The internal stint is sized and configured for placement within the interior volume of the natural heart 10, generally alongside the right side of the interventricular septum. The stint also includes at least two separate ring structures (not shown) for positioning proximate the valve annuli of the left side of the heart. Further details of suitable frameworks are set forth in U.S. Pat. No. 5,957,977, and pending U.S. patent application Ser. No. 09/850,554.

As illustrated in FIGS. 1A, 2A, and 3A, the framework also includes the external yoke 70 which is configured for placement around a portion of the exterior surface or epicardium of a natural heart 10. The generally stirrup-shaped yoke 70 in the illustrated embodiment restricts free motion of the natural heart 10 so that the natural heart 10 can be actuated and assisted. Yoke 70 also acts as an anchor for an appropriate actuator element or system for use with the invention. In one embodiment, the yoke 70 is between about 1 and 2 cm wide and includes a semi-rigid collar portion, preferably made of either a solid polymer of appropriate mechanical behavior, such as polypropylene or polyacetal, or a composite of metal (stainless steel or pure titanium) band or coil spring elements, polymer fabric and fiber (e.g. polyester knit) and soft elastomer, for providing rigidity to the yoke 70. Additionally, the yoke 70 may include a gel-filled cushion portion 80 that is positioned immediately adjacent the exterior surface (epicardium) of the natural heart 10 for providing equalized pressure over the irregularities in the epicardial surface of the heart 10, and any of the coronary arteries 30 within a region under the yoke 70. Preferably, the yoke 70 is sized and configured for placement adjacent at least a portion of the atrioventricular groove 22, and simultaneously adjacent at least a portion of the anterior and posterior portions of the interventricular groove 20, and most preferably, adjacent at least a substantial portion of the anterior and posterior portion of the interventricular groove 20, as shown in FIGS. 1A, 2A, and 3A.

General alignment of the yoke 70 with interior framework elements is maintained by at least one transmural cord (not shown), and preferably, a plurality of cords that penetrate the walls of the natural heart 10 and connect to the internal stint and one or more of the internal rings, as noted above and discussed in U.S. Pat. No. 5,957,977.

Referring now to FIG. 1A, an actuation system 82 is illustrated for assisting the operation of the natural heart 10. The actuation system 82 incorporates a framework for interfacing with the natural heart, as discussed above. One visual external element of a suitable framework is the yoke 70, as illustrated in FIG. 1A. Yoke 70 is anchored to tissue of the heart, such as through an internal framework element or elements, as discussed above. The yoke element 70 is anchored in position on heart 10 to provide support for an actuator device or element. As illustrated in the figures, the actuation system of the invention, and particularly the protective sheath 84, are shown coupled to the left ventricle of the heart. However, as will be understood by a person of ordinary skill in the art, the invention may be utilized with other chambers of the heart, such as the left atrium, or the right side of the heart, including the right atrium and/or the right ventricle. Therefore, the invention is shown positioned for the purposes of illustration only, and its illustrated position is not meant to be limiting to the usefulness of the invention.

Figure 1B:
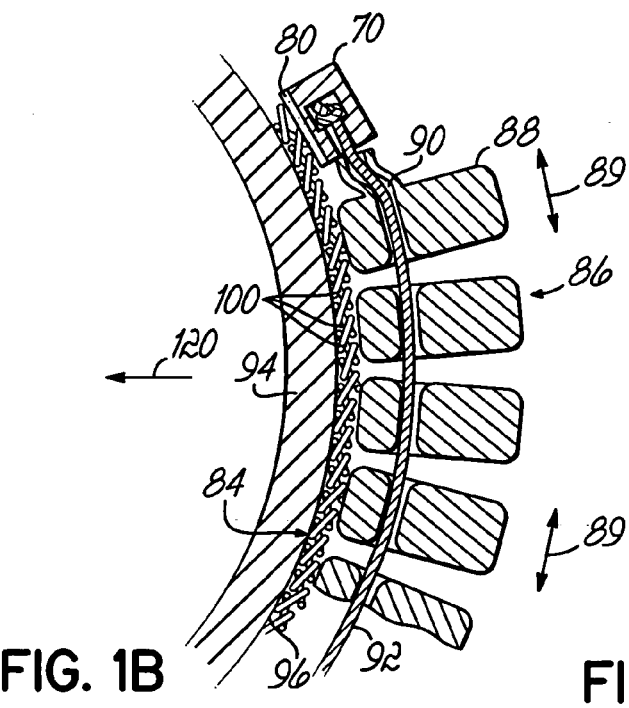
FIGS. 1B and 1C are cross-sectional views which illustrate the embodiment of the invention shown in FIG. 1A with a heart wall actuation system in a relaxed and an actuated state, respectively.
Figure 1C:
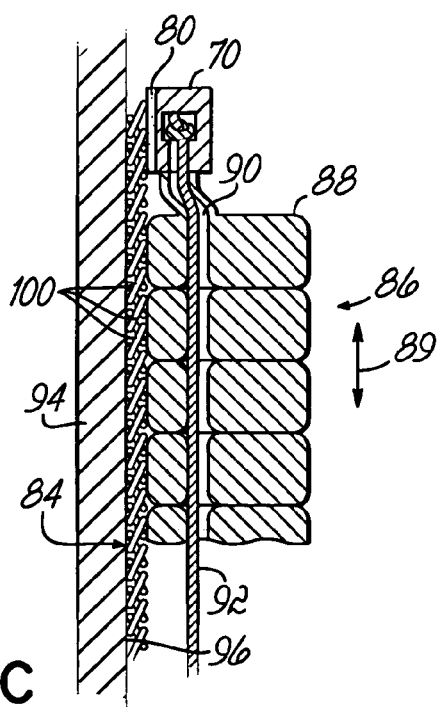

For actuating a wall of the heart, such as to cyclically deform or shape the wall of the heart, change the volume of a heart chamber, and assist in the pumping action, the actuator system includes an actuator element or device which is adapted to be coupled to the framework, such as yoke 70. One possible actuator element 86 is shown in the Figures, but is not meant to be limiting. The actuator element 86 is configured for extending along, or proximate to, a portion of the heart wall exterior surface, such as the exterior surface 96 of the left ventricle. Actuator element 86 is operable for indenting or shaping the portion of the heart wall to effect a reduction in the volume of the heart and thereby assist in the pumping of blood through the heart. In the illustrated embodiment, the actuator element 86 comprises an actuator band extending along a portion of the heart wall and selectively movable between a relaxed state and an actuated state, as illustrated in FIGS. 1B and 1C, respectively. When in the actuated state, the band 86 assumes a predetermined shape, as illustrated in FIG. 1C, and thereby indents the protective sheath 84 of the invention, and indents a portion of the heart wall underlying the protective sheath to affect a reduction in the volume of the heart for a particular heart chamber (e.g., the left ventricle). Actuator band 86 includes a plurality of juxtaposed blocks 88 configured to be drawn together and to cooperate with each other, when drawn together, to assume a predetermined shape. In the Figures, and particularly FIGS. 1C, 2C, and 3C, the band is shown to take a generally flat shape in contrast to the relaxed curved shape which follows the natural curves of the heart. However, the band might be made to take various shapes when actuated, as shown in U.S. patent application Ser. No. 09/850,554.

For actuating the element 86, the blocks include a passage 90 formed therethrough, made up of individual passages through the respective blocks 88. A cable structure 92 extends through the passage and is coupled at one end to an anchor point, such as to the framework element, or yoke 70. Drawing cable 92 through the passage 90 draws the blocks together so that the blocks cooperate with each other as illustrated in FIG. 1C, to assume the desired predetermined shape of the actuated band. The band 86 acts on the heart wall and indents the heart wall to effect a reduction in volume of the heart chamber. For example, band 86 may provide an inward force on the heart wall. As shown between FIGS. 1B and 1C, the actuator blocks 88 also slide or move along the heart wall surface in the actuated state. This presents a fixation force on the heart wall, generally normal to the wall surface 96. Such an actuator system is illustrated in greater detail in U.S. patent application, Ser. No. 09/850,554.

In accordance with another aspect of the present invention, protective sheath 84 is configured to extend along a portion of the heart wall, such as the outer wall of the left ventricle, as illustrated in the figures. The protective sheath 84 extends along the wall and is positioned between the actuator element 86 and the heart wall surface 96 for protecting the heart wall surface 96 from damage by the actuator element. The protective sheath is flexible, and is operable to transmit, to the heart wall portion, a force thereon by the actuator element for indenting the heart wall portion. More specifically, in the illustrated embodiment of the actuator element 86, the blocks 88 move against heart wall portion 94 as the actuator element moves between a relaxed and actuated position. The heart wall portion 94 and tissue associated therewith, are forcibly indented and deformed due to the action of the actuator element 86. Furthermore, friction exists between heart wall portion 94 (i.e., surface 96) and the moving blocks 88. The protective sheath 86 protects the tissue of the heart wall portion 94 to prevent damage of that tissue. Simultaneously, the forces for shaping and deforming the wall portion 94 are transmitted through the flexible protective sheath 84. The sheath provides a paving feature which absorbs the friction of the movement of the actuator elements, such as the individual blocks 88, and protects the heart surface 96 from abrasion, pinching, or other trauma associated with the action of the actuator element 86. For example, pinching of the heart wall tissue may be a specific concern with the actuator element 86 illustrated herein.

The protective sheath also helps to blunt any trauma to the heart tissue caused by the actuator element and helps spread the indenting forces smoothly over the heart wall surface 96.

In one embodiment of the invention, the protective sheath 84 is generally porous and may include openings which encourage the ingrowth of a layer of flexible fibrous, or scar tissue, which intermeshes with sheath 84 and extends the overall protective effect of the invention.

FIGS. 1A-1C illustrate one particular embodiment of the invention. Specifically, the protective sheath 84 includes a plurality of interlocked elements 100. As illustrated in FIG. 1A, the interlocked elements 100 essentially form individual ring structures, as illustrated by reference numeral 102. In such an embodiment, the protective sheath 84 resembles "chain-mail" armor which may move freely in all directions so that the heart may be actuated readily in all directions.

The protective sheath 84 may be held in position on the heart with tissue adhesives, sutures, or other means commonly used for tissue-to-prosthesis fixation. That is, it may be just wrapped around the heart. Alternatively, the sheath 84 may be fixed to a framework element, such as yoke 70 and/or to the actuator element 86. The material making up the interlocked elements 100 may be formed of a suitable metal, such as stainless steel 316 or CP titanium, for providing low friction and wear resistance. An alternative material for the interlocked elements 100 might include a ceramic, highly abrasion-resistant polymer, such as polyacetal (e.g., a material often referred to as Delrin™) or polyethylene, particularly ultra-high molecular weight polyethylene, or UHMWFE. Other materials may be nickel-titanium alloys or other shape memory components, such as, for example, Nitinol™. Alternatively, the interlocked elements might be formed of a combination of such materials wherein alternating elements are made of different materials.

Figure 2B:
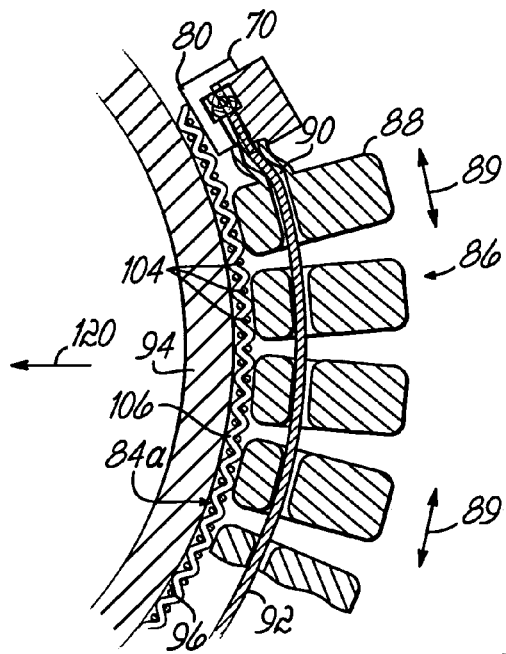
FIGS. 2B and 2C are cross-sectional views which illustrate the alternative embodiment of the invention shown in FIG. 2A with a heart wall actuation system in a relaxed and an actuated state, respectively.
Figure 2C:
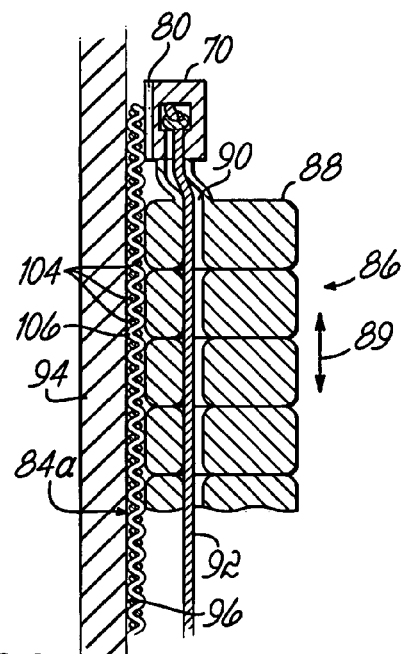

FIGS. 2A, 2B, and 2C illustrate another embodiment of the invention, and are illustrated similarly to FIGS. 1A-1C. That is, FIG. 2A shows the alternative embodiment of the protective sheath mounted on a human heart with a suitable framework. FIGS. 2B and 2C illustrate one possible actuator element to be utilized with the protective sheath, in both a relaxed and actuated position, respectively. Similar reference numerals are utilized for similar elements previously described in FIGS. 1A-1C.

Protective sheath 84a includes a net of woven or knit, abrasion-resistant cords or threads. As illustrated in FIG. 2B, for example, transverse cords 104, cooperate with longitudinal cords 106 to form the net. The net might be woven or knitted in various other suitable ways known to those of ordinary skill in the art, and the embodiment of the invention is not limited to the woven structure illustrated in the drawings. Protective sheath 84a provides an abrasion-resistant net for protecting the tissue of the heart, as discussed above, while providing the translation of necessary forces to the heart from the actuation system. The actuator element 86, and particularly the blocks 88 may readily move on the net 84a for forming and shaping the heart wall portion 94. As noted, the woven net 84a provides a paving action and absorbs friction of movement of the blocks 88 while protecting the heart surface 96 from abrasion, pinching, and other trauma.

In one embodiment of the invention, the net 84a is formed of cords 104, 106 which are made of an abrasion resistant material, such as a suitable metal, including stainless steel 316 or CP titanium, nickel-titanium alloys, ceramics, or shape memory materials. Another suitable material for the cords 104, 106 forming the protective net 84a is an abrasion resistant polymer, such as linearly crystalline polyethylene, sometimes referred to by the trademark Spectra™. A combination of the various materials might also be used.

In one embodiment, the cables or cords (e.g. cords 106) on the actuator-facing surface, or their component fibers, are oriented parallel to the direction of tangential motion of the actuator element 86, such as the motion of blocks 88. For example, referring to FIGS. 2B and 2C, the block 88 would generally move tangentially in the direction of arrows 89 when actuated. With the cords 106 oriented generally parallel with that direction, friction may be reduced to make a smoother surface. This may, in turn, reduce both material damage from wear and energy loss from friction. The cords may be so oriented using available textile design and manufacturing techniques as known to those of ordinary skill in the art. While the actuator 86 of the Figures shows one possible embodiment, other embodiments might have elements moving in other tangential directions than direction 89. In accordance with the invention, other cords, such as cords 104, might be oriented generally parallel to such other tangential motion.

FIGS. 3A, 3B, and 3C illustrate another alternative embodiment of the invention, and like reference numerals are utilized for like elements, as discussed above.

A protective sheath 84b includes a fabric jacket 108, with a plurality of studs 110 interspersed throughout the fabric jacket 108. Referring to FIGS. 3B and 3C, the studs 110 have stud surfaces 112a, 112b on either side thereof, and the stud surfaces are generally co-extensive with surfaces of the fabric 108. In that way, the combination of fabric jacket and studs forms an overall protective sheath 84b. In accordance with one aspect of the present invention, the surfaces 112a of the studs, which are positioned away from the heart, are rounded. With the outer rounded surfaces 112a, the blocks 88 of the actuator element 86 slide freely over the protective sheath 84b and the sheath prevents damage to the heart tissue associated with the actuation of the heart wall.

Suitable materials for the studs include suitable metals, such as stainless steel 316 or CP titanium. A ceramic, such as pyrolytic carbon would also be suitable. Furthermore, a wear-resistant polymer, such as a polyacetal (e.g., Delrin™, as noted above) or ultra-high molecular weight polyethylene (UHMWPE) may also be utilized.

The fabric jacket may be formed of a biocompatible material, such as a woven, knit, or braided material of polyester, linearly crystalline polyethylene (Spectra™), or polytetrafluoroethylene. Alternatively, an absorbable polymeric fabric, such as an oxidized cellulose or polyglycolic acid might be utilized.

The protective sheath 84b operates similarly to the other embodiments of the protective sheath discussed above to translate forces in motion of the actuator element to heart wall portion 94 without damaging the tissue of heart surface 96.

The present invention provides a significant benefit when utilized with heart wall actuating elements and systems by providing a protective paving structure which allows elements of the heart wall actuating system to slide on the surface of the heart in the directions which are generally tangent to the surface 96 of the heart wall and the surface created by the protective sheath. Simultaneously, the protective sheath is flexible, and is operable to transmit any translational or inward movement of the actuator elements in directions which have force components generally normal to the heart surface 96 and normal to the protective sheath, such as in the direction of reference arrow 120 in FIG. 1B.

The protective sheath of the invention may be anchored to the framework, such as framework element 70 for providing the desired protection of the heart wall which is being actuated. Alternatively, as noted above, the protective sheath could be individually coupled, such as by adhesive or sutures to the heart wall.

The porosity of the protective sheath is a desirable characteristic, as it may allow and/or encourage ingrowth of a layer of a flexible, fibrous or scar tissue with the protective sheath which expands and extends the protective effect of the invention. However, the growth of such a layer is not critical to the invention, as the invention alone will provide the desired protection of the actuated heart wall.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. An actuation system for assisting the operation of a human or animal heart, the actuation system comprising:
    an actuator element configured for extending proximate and exterior to a portion of a heart wall and operable for moving and actively indenting that portion of said heart wall to actively effect a reduction in the volume of the heart;
    a passive protective sheath positioned independent of the actuator element on the heart wall and configured to extend along the heart wall between the moving actuator element and the heart wall portion for protecting the heart wall portion from damage by the moving actuator element;
    the passive protective sheath including a fabric jacket and a plurality of studs interspersed throughout the fabric and having stud surfaces generally coextensive with surfaces of the fabric;
    the passive protective sheath being flexible and operable to transmit, to the heart wall portion, a moving force thereon by the moving actuator element for actively indenting the heart wall portion.

2. The actuation system of claim 1 further comprising a framework for interfacing with the heart and including elements configured for being anchored to the heart.

3. The actuation system of claim 1, wherein the protective sheath is porous.

4. The actuation system of claim 1, wherein said studs have rounded surfaces on at least one surface of the fabric.

5. The actuation system of claim 1, wherein the studs are formed of at least one of stainless steel, titanium, a ceramic, an abrasion-resistant polymer and a combination of same.

6. The actuation system of claim 1, wherein the fabric jacket is formed of at least one of a polyester, PTFE, a cellulose, polyethylene, and polyglycolic acid.

7. The actuation system of claim 1 wherein the actuator element comprises:
    an actuator band extending along the portion of the heart wall, the actuator band being selectively movable between an actuated state and a relaxed state and operable, when in the actuated state, to assume a predetermined shape and thereby actively indent the protective sheath and the portion of the heart wall to dynamically effect a reduction in the volume of the heart.

8. The actuation system of claim 7 wherein the actuator band includes a plurality of juxtaposed blocks configured to be drawn together and to cooperate with each other, when drawn together, to assume the predetermined shape.

9. The actuation system of claim 2 wherein said protective sheath is anchored to said framework.

10. The actuation system of claim 1 wherein said protective sheath is configured for being anchored to tissue of a heart.

11. The actuation system of claim 2 wherein the actuator element is coupled to the framework.

12. A method for assisting the operation of a human or animal heart, the method comprising:
    positioning an actuator element to extend along and exterior to a portion of a heart wall the actuator operable for moving to act on the heart wall portion;
    positioning a passive flexible protective sheath that is independent of the actuator element along the heart wall between the moving actuator element and the heart wall portion for protecting the heart wall portion from damage;
    the passive protective sheath including a fabric jacket and a plurality of studs interspersed throughout the fabric and having stud surfaces generally coextensive with surfaces of the fabric;
    indenting the protective sheath and said portion of the heart wall with the actuator element to actively effect a reduction in the volume of the heart.

13. The method of claim 12 further comprising anchoring a framework to tissue of a natural heart and coupling the actuator element to the framework.

14. The method of claim 12 further comprising positioning an actuator band to extend along a portion of a heart wall, and manipulating the actuator band so the band takes a predetermined shape and actively indents the protective sheath and a portion of the heart wall.

15. The method of claim 14 wherein the actuator band includes a plurality of juxtaposed blocks, the method further comprising drawing the blocks together to make the band assume the predetermined shape.

16. The method of claim 12 further comprising anchoring the protective sheath to tissue of the heart.

17. The method of claim 13 further comprising anchoring the protective sheath to the framework.

* * * * *